US009820671B2

(12) United States Patent
Ignagni et al.

(10) Patent No.: US 9,820,671 B2
(45) Date of Patent: Nov. 21, 2017

(54) DEVICES AND METHODS FOR ASSESSING MOTOR POINT ELECTROMYOGRAM AS A BIOMARKER

(75) Inventors: Anthony R. Ignagni, Oberlin, OH (US); Raymond P. Onders, Shaker Heights, OH (US)

(73) Assignee: SYNAPSE BIOMEDICAL, INC., Oberlin, OH (US)

( * ) Notice: Subject to any disclaimer, the term of this patent is extended or adjusted under 35 U.S.C. 154(b) by 1604 days.

(21) Appl. No.: 12/122,482

(22) Filed: May 16, 2008

(65) Prior Publication Data

US 2008/0287820 A1 Nov. 20, 2008

Related U.S. Application Data

(60) Provisional application No. 60/938,686, filed on May 17, 2007.

(51) Int. Cl.
*A61B 10/00* (2006.01)
*A61B 5/0488* (2006.01)
*A61N 1/36* (2006.01)

(52) U.S. Cl.
CPC .......... *A61B 5/0488* (2013.01); *A61N 1/3601* (2013.01)

(58) Field of Classification Search
CPC .. A61B 5/0488; A61B 5/0492; A61B 5/04882
USPC ........................................... 600/546; 607/42
See application file for complete search history.

(56) References Cited

U.S. PATENT DOCUMENTS

| | | | |
|---|---|---|---|
| 1,693,734 A | 12/1928 | Waggoner |
| 2,532,788 A | 12/1950 | Sarnoff |
| 2,664,880 A | 1/1954 | Wales, Jr. |
| 4,699,875 A | 10/1987 | Appel |
| 4,773,393 A | 9/1988 | Haber et al. |
| 4,827,935 A | 5/1989 | Geddes et al. |
| 4,830,008 A | 5/1989 | Meer |

(Continued)

FOREIGN PATENT DOCUMENTS

| | | |
|---|---|---|
| EP | 996482 A1 | 5/2000 |
| EP | 873155 B1 | 6/2003 |

(Continued)

OTHER PUBLICATIONS

Zifko et al. Central and peripheral respiratory electrophysiological studies in myotonic dystrophy. Brain (1996); 119, 1911-1922.*

(Continued)

*Primary Examiner* — Daniel Cerioni
(74) *Attorney, Agent, or Firm* — Shay Glenn LLP

(57) ABSTRACT

Described herein are methods of detecting the presence or progression of neuromuscular disorders (including ALS) based at least in part on diaphragm EMG signals taken at different points in time from the same implanted electrode(s). Signals may be used to diagnose or to monitor progression of a disorder or to track a treatment. Thus, diaphragm EMG signal may be used as a marker (e.g., a "biomarker") for the detection or progression of a neurological disorder such as ALS. The characteristics or parameters of diaphragm EMG signals may be used to create an activity index, which may be output or compared and further analyzed. These signals may also be analyzed to show a difference between the left and right sides of the diaphragm.

28 Claims, 9 Drawing Sheets

(56) References Cited

U.S. PATENT DOCUMENTS

| | | |
|---|---|---|
| 4,863,438 A | 9/1989 | Gauderer et al. |
| 4,989,617 A | 2/1991 | Memberg et al. |
| 5,056,519 A | 10/1991 | Vince |
| 5,074,846 A | 12/1991 | Clegg et al. |
| 5,146,918 A | 9/1992 | Kallok et al. |
| 5,314,463 A | 5/1994 | Camps et al. |
| 5,368,035 A | 11/1994 | Hamm et al. |
| 5,429,636 A | 7/1995 | Shikhman et al. |
| 5,472,438 A | 12/1995 | Schmit et al. |
| 5,483,969 A | 1/1996 | Testerman et al. |
| 5,524,632 A | 6/1996 | Stein et al. |
| 5,527,358 A | 6/1996 | Mehmanesh et al. |
| 5,678,535 A | 10/1997 | DiMarco |
| 5,716,392 A | 2/1998 | Bourgeois et al. |
| 5,718,248 A | 2/1998 | Trumble et al. |
| 5,792,165 A | 8/1998 | Klieman et al. |
| 5,797,923 A | 8/1998 | Aiyar et al. |
| 5,813,399 A | 9/1998 | Isaza et al. |
| 5,814,086 A | 9/1998 | Hirschberg et al. |
| 5,849,290 A | 12/1998 | Brown et al. |
| 5,851,783 A | 12/1998 | Appel et al. |
| 6,035,856 A | 3/2000 | LaFontaine et al. |
| 6,194,217 B1 | 2/2001 | Matson |
| 6,198,970 B1 | 3/2001 | Freed et al. |
| 6,210,970 B1 | 4/2001 | Matson |
| 6,245,053 B1 | 6/2001 | Benjamin |
| 6,254,425 B1 | 7/2001 | Shchervinsky et al. |
| 6,311,692 B1 | 11/2001 | Vaska et al. |
| 6,321,109 B2 | 11/2001 | Ben-Haim et al. |
| 6,360,740 B1 | 3/2002 | Ward et al. |
| 6,397,108 B1 | 5/2002 | Camps et al. |
| 6,405,732 B1 | 6/2002 | Edwards et al. |
| 6,415,183 B1 | 7/2002 | Scheiner et al. |
| 6,463,327 B1 | 10/2002 | Lurie et al. |
| 6,477,423 B1 | 11/2002 | Jenkins |
| 6,571,127 B1 | 5/2003 | Ben-Haim et al. |
| 6,645,145 B1 | 11/2003 | Dreschel et al. |
| 6,845,271 B2 | 1/2005 | Fang et al. |
| 6,918,871 B2 | 7/2005 | Schulze |
| 6,947,792 B2 | 9/2005 | Ben-Haim et al. |
| 7,006,871 B1 | 2/2006 | Darvish et al. |
| 7,044,921 B2 | 5/2006 | Asmus et al. |
| 7,071,194 B2 | 7/2006 | Teng |
| 7,107,092 B2 | 9/2006 | Goldstein et al. |
| 7,120,497 B2 | 10/2006 | Ben-Haim et al. |
| 7,155,278 B2 | 12/2006 | King et al. |
| 7,165,551 B2 | 1/2007 | Edwards et al. |
| 7,195,881 B2 | 3/2007 | Geffard |
| 7,206,636 B1 | 4/2007 | Turcott |
| 7,207,946 B2 | 4/2007 | Sirokman |
| 7,221,978 B2 | 5/2007 | Ben-Haim et al. |
| 7,225,016 B1 | 5/2007 | Koh |
| 7,329,489 B2 | 2/2008 | Kaddurah-Daouk et al. |
| 7,356,521 B2 | 4/2008 | Wang et al. |
| 7,418,298 B2 | 8/2008 | Shiroff et al. |
| 2001/0025177 A1 | 9/2001 | Woloszko et al. |
| 2001/0049497 A1 | 12/2001 | Kalloo et al. |
| 2002/0103424 A1 | 8/2002 | Swoyer et al. |
| 2003/0040785 A1 | 2/2003 | Maschino et al. |
| 2003/0148404 A1 | 8/2003 | Michaelson |
| 2003/0171672 A1 | 9/2003 | Varghese et al. |
| 2003/0175832 A1 | 9/2003 | Marton et al. |
| 2003/0195600 A1 | 10/2003 | Tronnes et al. |
| 2004/0003813 A1 | 1/2004 | Banner et al. |
| 2004/0044377 A1 | 3/2004 | Larsson |
| 2004/0064069 A1 | 4/2004 | Reynolds et al. |
| 2004/0122360 A1 | 6/2004 | Waldhauser et al. |
| 2004/0127954 A1* | 7/2004 | McDonald, III ............... 607/48 |
| 2004/0167437 A1 | 8/2004 | Sharrow et al. |
| 2004/0167442 A1 | 8/2004 | Shireman et al. |
| 2004/0167443 A1 | 8/2004 | Shireman et al. |
| 2004/0172090 A1 | 9/2004 | Janzig et al. |
| 2004/0177388 A1 | 9/2004 | Botas et al. |
| 2004/0254572 A1 | 12/2004 | McIntyre et al. |
| 2004/0260198 A1 | 12/2004 | Rothberg et al. |
| 2004/0260245 A1 | 12/2004 | Clem et al. |
| 2004/0260246 A1 | 12/2004 | Desmond |
| 2004/0260337 A1 | 12/2004 | Freed |
| 2005/0021102 A1 | 1/2005 | Ignagni et al. |
| 2005/0033394 A1 | 2/2005 | Seifert et al. |
| 2005/0042589 A1 | 2/2005 | Hatlestad et al. |
| 2005/0049523 A1 | 3/2005 | Crank |
| 2005/0054950 A1 | 3/2005 | Parins |
| 2005/0054951 A1 | 3/2005 | Parins |
| 2005/0054952 A1 | 3/2005 | Eskuri et al. |
| 2005/0080463 A1 | 4/2005 | Stahmann et al. |
| 2005/0085734 A1 | 4/2005 | Tehrani |
| 2005/0085865 A1 | 4/2005 | Tehrani |
| 2005/0085866 A1 | 4/2005 | Tehrani |
| 2005/0085867 A1 | 4/2005 | Tehrani et al. |
| 2005/0085868 A1 | 4/2005 | Tehrani et al. |
| 2005/0085869 A1 | 4/2005 | Tehrani et al. |
| 2005/0107781 A1 | 5/2005 | Ostrovsky et al. |
| 2005/0107812 A1 | 5/2005 | Starksen et al. |
| 2005/0107860 A1 | 5/2005 | Ignagni et al. |
| 2005/0109340 A1 | 5/2005 | Tehrani |
| 2005/0113710 A1 | 5/2005 | Stahmann et al. |
| 2005/0115561 A1 | 6/2005 | Stahmann et al. |
| 2005/0124917 A1 | 6/2005 | Skujins et al. |
| 2005/0137501 A1 | 6/2005 | Euteneuer et al. |
| 2005/0148026 A1 | 7/2005 | Bowser et al. |
| 2005/0148818 A1 | 7/2005 | Mesallum |
| 2005/0165457 A1 | 7/2005 | Benser et al. |
| 2005/0209653 A1 | 9/2005 | Herbert et al. |
| 2005/0240241 A1 | 10/2005 | Yun et al. |
| 2005/0277945 A1 | 12/2005 | Saadat et al. |
| 2006/0030894 A1 | 2/2006 | Tehrani |
| 2006/0035849 A1 | 2/2006 | Spiegelman et al. |
| 2006/0036294 A1 | 2/2006 | Tehrani |
| 2006/0041022 A1 | 2/2006 | Pasinetti |
| 2006/0068452 A1 | 3/2006 | Goldknopf et al. |
| 2006/0088862 A1 | 4/2006 | Lee |
| 2006/0115854 A1 | 6/2006 | Goldknopf et al. |
| 2006/0115855 A1 | 6/2006 | Goldknopf et al. |
| 2006/0115856 A1 | 6/2006 | Goldknopf et al. |
| 2006/0115867 A1 | 6/2006 | Goldknopf et al. |
| 2006/0121619 A1 | 6/2006 | Bowser |
| 2006/0122662 A1 | 6/2006 | Tehrani et al. |
| 2006/0130161 A1 | 6/2006 | Genain |
| 2006/0130833 A1 | 6/2006 | Younes |
| 2006/0142815 A1 | 6/2006 | Tehrani et al. |
| 2006/0149316 A1 | 7/2006 | DeVries et al. |
| 2006/0149334 A1 | 7/2006 | Tehrani et al. |
| 2006/0155222 A1 | 7/2006 | Sherman et al. |
| 2006/0155341 A1 | 7/2006 | Tehrani et al. |
| 2006/0160087 A1 | 7/2006 | McGrath et al. |
| 2006/0167523 A1 | 7/2006 | Tehrani et al. |
| 2006/0200004 A1 | 9/2006 | Wilk |
| 2006/0224209 A1 | 10/2006 | Meyer |
| 2006/0237023 A1 | 10/2006 | Cox et al. |
| 2006/0247729 A1 | 11/2006 | Tehrani et al. |
| 2006/0258667 A1 | 11/2006 | Teng |
| 2006/0281809 A1 | 12/2006 | Miller et al. |
| 2006/0282131 A1 | 12/2006 | Caparso et al. |
| 2006/0286167 A1 | 12/2006 | Staunton et al. |
| 2006/0287679 A1 | 12/2006 | Stone |
| 2007/0016172 A1 | 1/2007 | Charukhchian |
| 2007/0017809 A1 | 1/2007 | Goldknopf et al. |
| 2007/0021421 A1 | 1/2007 | Hampton |
| 2007/0021500 A1 | 1/2007 | Twyman et al. |
| 2007/0021795 A1 | 1/2007 | Tehrani |
| 2007/0038127 A1 | 2/2007 | Goldstein et al. |
| 2007/0049793 A1 | 3/2007 | Ignagni et al. |
| 2007/0054852 A1 | 3/2007 | Lin et al. |
| 2007/0072943 A1 | 3/2007 | Miller et al. |
| 2007/0078099 A1 | 4/2007 | McLaurin |
| 2007/0087000 A1 | 4/2007 | Walsh et al. |
| 2007/0087314 A1 | 4/2007 | Gomo |
| 2007/0098812 A1 | 5/2007 | Feinstein et al. |
| 2007/0117772 A1 | 5/2007 | Bennett et al. |
| 2007/0118183 A1 | 5/2007 | Gelfand et al. |
| 2007/0122813 A1 | 5/2007 | Salomon et al. |
| 2007/0150006 A1 | 6/2007 | Libbus et al. |
| 2007/0150023 A1 | 6/2007 | Ignagni et al. |

(56) References Cited

U.S. PATENT DOCUMENTS

| | | | |
|---|---|---|---|
| 2007/0172820 | A1 | 7/2007 | Kaddurah-Daouk et al. |
| 2007/0191908 | A1 | 8/2007 | Jacob et al. |
| 2007/0196780 | A1 | 8/2007 | Ware et al. |
| 2007/0197932 | A1 | 8/2007 | Feke et al. |
| 2007/0202515 | A1 | 8/2007 | Hadlock et al. |
| 2007/0202537 | A1 | 8/2007 | Lingappa et al. |
| 2007/0221224 | A1 | 9/2007 | Pittman et al. |
| 2007/0225261 | A1 | 9/2007 | Miller et al. |
| 2007/0240718 | A1 | 10/2007 | Daly |
| 2007/0250162 | A1 | 10/2007 | Royalty |
| 2007/0265611 | A1 | 11/2007 | Ignagni et al. |
| 2007/0274992 | A1 | 11/2007 | Michalovich et al. |
| 2007/0282388 | A1 | 12/2007 | Sandyk |
| 2007/0292403 | A1 | 12/2007 | Nivaggioli |
| 2007/0292410 | A1 | 12/2007 | Cashman et al. |
| 2007/0298998 | A1 | 12/2007 | Paige et al. |
| 2008/0003208 | A1 | 1/2008 | Nivaggioli |
| 2008/0097153 | A1 | 4/2008 | Ignagni et al. |
| 2008/0121231 | A1* | 5/2008 | Sinderby et al. ........ 128/204.21 |
| 2008/0125828 | A1 | 5/2008 | Ignagni et al. |
| 2011/0060381 | A1 | 3/2011 | Ignagni et al. |
| 2013/0218231 | A1 | 8/2013 | Ignagni et al. |
| 2013/0238053 | A1 | 9/2013 | Ignagni et al. |

FOREIGN PATENT DOCUMENTS

| | | |
|---|---|---|
| EP | 1634617 A1 | 3/2006 |
| EP | 1653863 A2 | 5/2006 |
| EP | 1658020 A1 | 5/2006 |
| EP | 1660177 A1 | 5/2006 |
| EP | 1663370 A2 | 6/2006 |
| EP | 1667757 A2 | 6/2006 |
| EP | 1670611 A2 | 6/2006 |
| EP | 1684655 A2 | 8/2006 |
| EP | 1393773 B1 | 10/2006 |
| EP | 1306104 B1 | 1/2007 |
| EP | 1205202 B1 | 6/2007 |
| WO | WO 86/00234 A1 | 1/1986 |
| WO | WO 2005/039691 A1 | 5/2005 |
| WO | WO 2005/044079 A2 | 5/2005 |
| WO | WO 2006/062710 A1 | 6/2006 |
| WO | WO 2006/079152 A1 | 8/2006 |
| WO | WO 2006/083675 A2 | 8/2006 |
| WO | WO 2006/088696 A2 | 8/2006 |
| WO | WO 2006/121447 A2 | 11/2006 |
| WO | WO 2006/124023 A1 | 11/2006 |
| WO | WO 2006/131150 A1 | 12/2006 |
| WO | WO 2006/138069 A1 | 12/2006 |
| WO | WO 2007/035804 A2 | 3/2007 |
| WO | WO 2007/053230 A2 | 5/2007 |
| WO | WO 2007/058780 A2 | 5/2007 |
| WO | WO 2007/058938 A2 | 5/2007 |
| WO | WO 2007/061902 A2 | 5/2007 |
| WO | WO 2007/082384 A1 | 7/2007 |
| WO | WO 2007/103585 A2 | 9/2007 |
| WO | WO 2007/109443 A2 | 9/2007 |
| WO | WO 2007/128002 A2 | 11/2007 |

OTHER PUBLICATIONS de Carvalho et al. Medicl technology assessment: Electrodiagnosis in motor neauron diseases and amyotrophic lateral sclerosis. Neurophysiol Clin. 2001; 31: p. 341-348.*

Ignagni et al.; U.S. Appl. No. 12/261,979 entitled "Method of improving sleep disordered breathing," filed Oct. 30, 2008.

Ignagni et al.; U.S. Appl. No. 12/690,410 entitled "Device and Method of Neuromodulation to Effect a Functionally Restorative Adaption of The Neuromuscular System," filed Jan. 20, 2010.

Kalloo et al; Flexible transgastric peritoneoscopy: a novel approach to diagnosis and therapeutic intervention in the peritoneal cavity; Gastrointestinal Endoscopy; vol. 60; No. 1; pp. 114-117; 2004.

Ignagni et al; U.S. Appl. No. 12/026,428 entitled "Removeable intramuscular electrode," filed Feb. 5, 2008.

Ayas et al; Prevention of human diaphragm atrophy with short periods of electrical stimulation; Am J Respir Crit Care Med; vol. 159; pp. 2018-2020; 1999.

Bhadra et al.; Extraction force and tissue change during removal of a tined intramuscular electrode from rat gastrocnemius; Annals of Biomedical Engineering; vol. 34; No. 6; pp. 1042-1050; Jun. 2006.

DeCarvalho et al.; Motor neuron disease presenting with respiratory failure; Journal of the Neurological Sciences; vol. 139; no. Suppl.; 1996; pp. 117-122.

DiMarco et al.; Phrenic nerve pacing in a tetraplegic patient via intramuscular diaphragm electrodes; American Journal of Respiratory and Critical Care Medicine; vol. 166 (12 Pt 1); pp. 1604-1606; Dec. 15, 2002.

DiMarco A. F.; Restoration of respiratory muscle function following spinal cord injury—Review of electrical and magnetic stimulation techniques; Respiratory Physiology & Neurobiology; 147; 273-287; 2005.

Knutson et al.; Electrode fracture rates and occurrences of infection and granuloma associated with percutaneous intramuscular electrodes in upper-limb functional electrical stimulation applications; Journal of Rehabilitation Research and Development; vol. 39; No. 6; pp. 671-684, Nov./Dec. 2002.

Nochomovitz et al.; Conditioning of the diaphragm with phrenic nerve stimulation after prolonged disuse; American Review of Respiratory Disease; vol. 130; No. 4; 325-329; Oct. 1984.

Nochomovitz et al.; Diaphragm activation with intramuscular stimulation in dogs; American Review of Respiratory Disease; vol. 127; No. 3; 685-687; Mar. 1983.

Onders et al.; Early results of laparoscopic motor point diaphragm pacing in amyotrophic lateral sclerosis; Amyotrophic Lateral Sclerosis (Abstracts from the 16th Intl. Symp. ALS/MND; vol. 6, supp. 1; ISSN1743-4475; pp. 142-143; Dec. 2005.

Onders et al.; Mapping the phrenic nerve motor point: the key to a successful laparoscopic diaphragm pacing system in the first human series; Surgery; vol. 136; No. 4; 819-26; Oct. 2004.

Peterson et al.; Long-term intramuscular electrical activation of the phrenic nerve: Safety and reliability; IEEE; vol. 41; No. 12; pp. 1115-1126; Dec. 1994.

Peterson et al.; Electrical activation of respiratory muscles by methods other than phrenic nerve cuff electrodes; Pacing and Clinical Electrophysiology; vol. 12; No. 5; pp. 854-878; May 1989.

Peterson et al.; Intramuscular electrical activation of the phrenic nerve; IEEE Transactions on Biomedical Engineering; vol. BME-33; No. 3; 342-351; Mar. 1986.

Polkey et al.; Influence of acute lung volume change on contractile properties of human diaphragm; Journal of Applied Physiology; vol. 85, No. 4; pp. 1322-1328; Oct. 1998.

Sarnoff et al.; Electrophrenic respiration; Science; vol. 108; 482; Oct. 29, 1948.

Schmit, et al.; Laparoscopic placement of electrodes for diaphragm pacing using stimulation to locate the phrenic nerve motor points; IEEE Trans on Rehab Engineer; vol. 6; No. 4; 382-390; Dec. 1998.

Stewart et al.; Electromyography of respiratory muscles in amyotrophic lateral sclerosis; Journal of the Neurological Sciences; vol. 191; No. 1-2; Oct. 15, 2001; pp. 67-73.

McGee et al.; A reliable method for monitoring intraabdominal pressure during natural orifice translumenal endoscopic surgery; Surg Endosc.; 21(4): pp. 672-676; Apr. 2007.

Onders, Raymond P.; The Utility of Flexible Endoscopy During Advanced Laparoscopy; Seminars in Laparoscopic Surgery; vol. 10, No. 1; pp. 43-48; Mar. 2003.

D'Honneur et al.; Comparison of the effects of mivacurium on the diaphragm and geniohyoid muscles; British Journal of Anesthesia; 77(6); pp. 716-719; Dec. 1996.

* cited by examiner

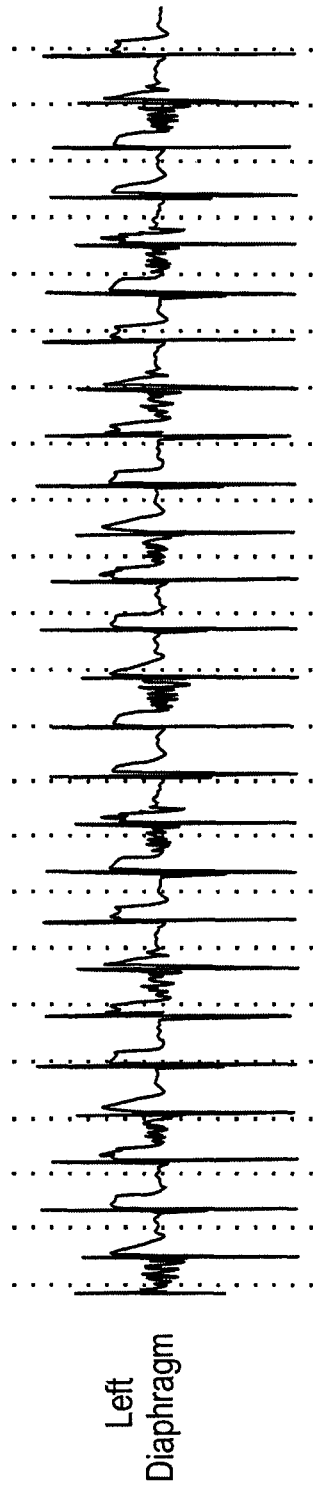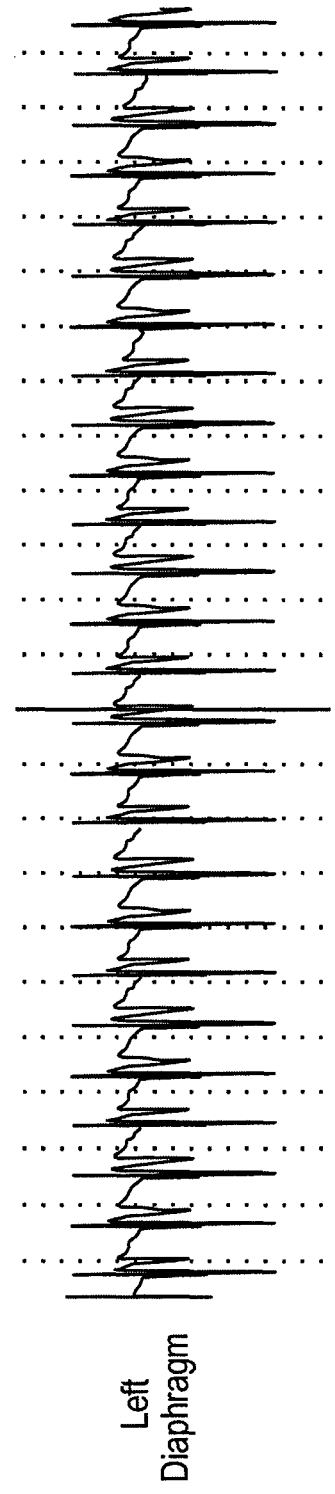

DEVICES AND METHODS FOR ASSESSING MOTOR POINT ELECTROMYOGRAM AS A BIOMARKER

CROSS-REFERENCE TO RELATED APPLICATIONS

This application claims priority to U.S. Provisional Patent Application No. 60/938,686, titled "Devices and Methods for Assessing Motor Point Electromyogram as a Biomarker", as filed on May 17, 2007.

This application is also related to U.S. patent application Ser. No. 12/026,428, filed on Feb. 5, 2008, which claims priority to U.S. Provisional Patent Application No. 60/899,799 filed on Feb. 5, 2007 (titled "Intramuscular Electrode").

INCORPORATION BY REFERENCE

All publications and patent applications mentioned in this specification are herein incorporated by reference to the same extent as if each individual publication or patent application was specifically and individually indicated to be incorporated by reference.

FIELD OF THE INVENTION

The invention is related to devices and methods for diagnosing disease and tracking the progression of disease, particularly neurodegenerative disease.

BACKGROUND OF THE INVENTION

Biomarkers may be used to monitor and treat progression of a disease or disorder. A biomarker has traditionally been a biochemical molecule whose presence and level is established as being closely and specifically related to a particular aspect of biological function or a disease process, and for which methods of reliable and quantifiable measurements have been developed. As applied to disease, biomarkers can be useful for the sensitivity they bring to a diagnostic process, where their presence can detect disease at an early stage, or when other clinical manifestations of the disease are not fully manifested, such that diagnosis can be difficult. Inasmuch as biomarkers can be used to monitor a disease once it has been diagnosed, they can be used to measure the effectiveness of treatments for the disease. Often, it takes time for treatment to allow easily observable clinical improvement, and thus, as with diagnosis, a biomarker can provide an indication of treatment effectiveness before clinical improvement is obvious. Additionally, clinical indications of improvement can be difficult to quantify, and can be masked by clinical factors not directly tied to the disease. Thus, biomarkers are useful in detecting in effectiveness of treatment, as in determining, for example, the effectiveness of a drug, or any form of physical or electrical intervention.

Amyotrophic lateral sclerosis is difficult to diagnose at an early stage, and it is difficult to discern the rate of progression of disease, especially once therapy has been initiated. For some time, there has been a concerted effort to identify benchmarks or biomarkers useful in detecting the presence of ALS and the rate of its progression. To provide the basic features of biomarkers, such as being closely and specifically associated with the disease, and being quantifiable, a biomarker need not necessarily be a particular molecule. An effective biomarker may, for example, simply be a physiological measurement of a parameter that closely and specifically varies or manifests as a function of the presence or severity of the disease.

A number of physiologically measured or qualitatively assessed parameters have been investigated as biomarkers (benchmarks) for their ability to predict survival in ALS patients or as a surrogate predictor of disease progression. There are currently no biomarkers exclusively associated with ALS, or directly tied to the aspects of the disease process that underlie the clinical status of the patient and especially markers having sufficient sensitivity or resolution with regard to changes in the level of the disease. There is a need, therefore, for effective biomarkers for ALS, particularly those that are closely and specifically associated with the disease, that are quantifiable, that are cost-effective, that can be processed quickly into useful data, and that can be easily worked into the ongoing context of patient care.

The methods, devices and systems described herein have been developed from the surprising observation that the electromyographic measurements made from the same location of the same patient's diaphragm over time can provide a remarkably sensitive measure of the presence or progression of ALS, and the efficacy of treatment of ALS. Although the initial observations were made in ALS patients, the methods, devices and systems described may be applied to other neurological (neurodegenerative) diseases and disorders.

SUMMARY OF THE INVENTION

Described herein are devices and methods of applying the devices to identify and monitor the progress of neurological disease based on electromyographic (EMG) information from muscles affected by the disease. In particular, the methods make use of electromyographic activity of the diaphragm as a benchmark or marker ("biomarker") for the presence or level of a neurological disorder, including a neurodegenerative disorder such as ALS, or a centrally-mediated disorder such as sleep apnea. As a biomarker that provides information reflective of the level or severity of a disease, the method can be used to track the progression of the disease over time, and if the patient is being treated for the disease, the method can be informative as to the effectiveness of the treatment. Informative aspects of EMG signals from the diaphragm include the amplitude of the signal. For example, a decrease in the amplitude over time represents weakening of the diaphragm and progression of the disease, whereas stabilization of amplitude that had been decreasing prior to initiation of treatment may reflect effectiveness of the treatment. The method may also be applied to localize focal areas of the disease, as for example, the EMG can detect in amplitude of signals between the left and right sides of the diaphragm.

In the case of ALS, embodiments of the method may predict or quantify the inability of the diaphragm to contract, which is the single most serious manifestation of the disease. The method may demonstrate the presence or progression of ALS by comparing the diaphragm EMG signal measured from long-term implanted electrodes over extended periods of time. Implanted electrodes in the diaphragm are in the same position, thus minimizing variations inherent in measurements taken from electrodes placed for short term observation, or from electrodes placed on the body surface, which are patient to reading that vary according to their implanted position, the posture of the patient, and variations in temperature. Taking EMG measurements from the same implanted electrodes provides a strong control over variation inherent in placement, and thus a stability of background variables, allowing the collection of signal data that varies primarily by virtue of the progression of the disease over extended periods of time.

In particular, described herein are systems for diagnosing or tracking the progression or treatment of a neurological disorder that affects the function of a diaphragm. These systems may include an implantable diaphragm electrode and an analyzer unit for processing EMG signals from the implantable diaphragm electrode at different times and determining an activity score based on the EMG signals. The analyzer unit typically includes index-determining logic configured to determine at least one characteristic of an EMG signal and generate an activity index based on the EMG signal characteristic(s), a memory configured to store one or more activity index, and a comparator configured to compare a plurality of activity indexes and determine an activity score based on the comparison.

The system may also include an output configured to present the activity score determined by the analyzer unit. A controller may also be included as part of the system. The controller may be configured to control acquisition of EMG signals from the implantable diaphragm electrodes at different times. The controller may be part of the analyzer unit, or may communicate with the analyzer unit. The controller may also include user inputs, a timer, and automatic control logic (e.g., control logic) to trigger measurement of EMG signals and coordinate outputs.

The implantable diaphragm electrode used may include an anchor for securing the electrode in communication with a diaphragm. For example, the anchor may comprise a barb. Other examples of electrodes may be found, for example, in U.S. patent application Ser. No. 12/026,428, "REMOVABLE INTRAMUSCULAR ELECTRODE" (filed on Feb. 5, 2008). Electrodes may be monopolar, bipolar, or multipolar (e.g., tripolar).

The system may also include one or more sensors (e.g., patient sensors), wherein the sensor is configured to measure one or more of: tidal volume, airway pressure, or abdominal pressure, or the like.

The index-determining logic of the analyzer is configured to generate an activity index based on the EMG signal characteristic(s) and input from the sensor. The index-determining logic may be software, hardware, or some combination thereof. The index generated by the index-determining logic may be a numeric index (e.g., a calculation based on one or more measurements from the EMG and/or other inputs), or it may be a matrix of values. The index may be non-numeric (e.g., Boolean, qualitative, etc). Thus, the index analyzer unit may include a measuring unit for measuring at least one characteristic of an EMG signal and providing the measured characteristic to the index-determining logic. The measuring unit may be configured to measure at least one of: amplitude, frequency, power spectrum, time-to-peak rise time, relaxation time, compound action potential rise time, compound action potential fall time, fast twitch muscle contribution, and slow-twitch muscle contribution. Any of these parameters may be measured from the EMG. The duration of the EMG recorded may be predetermined (e.g., for one respiratory cycle or a portion of a cycle, or for some number of cycled), or for x seconds or minutes. or it may be based on a triggering event. For example, the system may sample each EMG until a parameter is measured with sufficient confidence (e.g., such that the variability is below a predetermined confidence level). In some variations, the recording of EMG from the electrode is continuous. Sampling from a continuous recording may be based on a "windowing" of a certain time, or based on an analysis of variation in the signal over time.

Also described herein are methods of diagnosing or tracking the progression or treatment of a neurological disorder that affects the function of a diaphragm. For example, in one variation, the method includes the steps of measuring a first EMG signal at an initial recording time from one or more electrodes implanted in a diaphragm, measuring a second EMG signal from the same one or more electrodes at a later recording time, and comparing the first EMG signal and the second EMG signal.

The disorder tracked or diagnosed may be any of a centrally-mediated breathing disorder or a neurodegenerative disease, including (but not limited to) apneas, ALS, etc.

The comparing step my include comparing one or more of the following EMG parameters: amplitude, frequency, power spectrum, time-to-peak rise time, relaxation time, compound action potential rise time, compound action potential fall time, fast twitch muscle contribution, and slow-twitch muscle contribution.

In some variations, the method also includes the step of mapping the diaphragm to determine an active region of the diaphragm and implanting the one or more electrodes at an active region of the diaphragm. Mapping may be particularly helpful (or even necessary) in ALS patients, or those suffering from disorders in which portions of the diaphragm are damaged or otherwise inactive or less active. Thus, the electrode(s) may be implanted in regions that are electrically active. In some variations, the mapping step may be used to map the diaphragm to determine a phrenic nerve motor point of the diaphragm. This is described in greater detail below. One or more electrodes may be implanted at the phrenic nerve motor point. The mapping step may include applying electrical stimuli to an area of diaphragm surface and identifying a site within the area that provokes a maximal physiological response to the stimuli.

In general, the mapping step may include observing a physiological response to the stimuli, including observing any of: abdominal pressure or airway pressure, and diaphragm contraction. These observations may provide feedback on the activity of the diaphragm.

The step of measuring the EMG signal (e.g., the first or later EMG signals) may include selecting a duration and/or period of time for recording (collecting) the signal, as mentioned above, and quantifying at least one characteristic of the EMG signal over the selected time. For example, a controller may determine the start of recording, and also the duration of the EMG recording collected. The EMG signal may be analyzed to determine values for one or more parameters. This analysis may be real-time (as it is being recorded) or after the recording has occurred. The time duration of collection of the EMG signal may be predetermined (e.g., preset) or may be variable or triggered. For example, the duration of recording may be for a single breath, for a particular number of breaths, or for a particular interval of time.

The EMG signal may be analyzed to determine one or more characteristic, which may be (or may be part of) an activity index. The characteristic of the EMG signal quantified may be selected from the group consisting of: amplitude, frequency, power spectrum, time-to-peak rise time, relaxation time, compound action potential rise time, compound action potential fall time, fast twitch muscle contribution, and slow-twitch muscle contribution.

The EMG signal may be filtered either during or after it is recorded. For example, the steps of measuring the first EMG signal and measuring the second EMG signal may include the step of filtering the EMG signals to remove or reduce electrical signals not arising from the diaphragm. Filtering may be analog (e.g., by filtering circuitry) or digital.

In some variations, the EMG signal may be correlated with a measurement of another physiological parameter. Thus, when determining an activity index, one or more parameters measured or determined from the EMG signal may be combined with one or more other physiological parameters. For example, the physiological parameter may be blood gas level, airway pressure, abdominal pressure, and abdominal movement.

Also described are methods of diagnosing or tracking the progression or treatment of a neurological disorder that affects the function of a patient's diaphragm that include the steps of determining a first activity index from a patient's diaphragm motor point EMG at a first time, determining a second activity index from the patient's diaphragm motor point EMG at a second time, comparing the first activity index and the second activity index, and characterizing the presence, progression or treatment of a neurological disorder based on the comparison between the first activity index and the second activity index.

As mentioned above, the method may also include the step of mapping the patient's diaphragm to determine a phrenic nerve motor point and/or implanting a diaphragm electrode in or adjacent to the patient's diaphragm at a phrenic nerve motor point.

First and second activity indexes may be determined based at least in part on one or more EMG parameter such as amplitude, frequency, power spectrum, time-to-peak rise time, relaxation time, compound action potential rise time, compound action potential fall time, fast twitch muscle contribution, and slow-twitch muscle contribution.

In some variations of the methods described herein, the activity indexes (e.g., first activity index, second activity index, etc.) are determined at least in part from EMG signals recorded while the patient is sleeping, or recorded during a volitional maneuver such as coughing, inhaling deeply and/or exhaling deeply, sniffing, or the like.

The step of determining the first activity index may include determining the first activity index from one or more parameter taken from the patient's diaphragm motor point EMG and also one or more additional respiratory parameter value, all taken at approximately the same time. Similarly, the step of determining the second activity index may determining the same values (EMG parameter values and respiratory parameter values) taken at a second (or around the second) time. Examples of non-EMG respiratory parameters may include tidal volume, airway pressure, abdominal movement, abdominal pressure, and blood gas level.

Also described are method of detecting the presence, progression or treatment of amyotrophic lateral sclerosis in a patient that include the steps of mapping the patient's diaphragm to determine an active region, implanting an intramuscular electrode at an active region in the patient's diaphragm, determining a first activity index from a diaphragm EMG detected by the implanted electrode at a first time, determining a second activity index from a diaphragm EMG detected by the implanted electrode at a second time, and determining the presence, progression, or treatment of amyotrophic lateral sclerosis based on a comparison between the first activity index and the second activity index.

As mentioned, the step of implanting comprises implanting the electrode on or near a phrenic nerve motor point. Also, the first and second activity indexes may be determined at least in part from estimates of one more of EMG parameters such as: amplitude, frequency, power spectrum, time-to-peak rise time, relaxation time, compound action potential rise time, compound action potential fall time, fast twitch muscle contribution, and slow-twitch muscle contribution.

BRIEF DESCRIPTION OF THE DRAWINGS

FIG. 6A shows the patient showing an EMG from the right diaphragm with a mean rectified amplitude of 49 μV at the initiation of therapy, and FIG. 6B shows the patient after 12 weeks of therapy, at which time the right diaphragm shows a mean rectified amplitude of 62 μV.

FIGS. 8A and 8B show electromyographic diaphragm activity (eDA) data from a patient prior to and after receiving non-invasive ventilatory therapy. FIG. 8A shows data from the patient (who is not on non-invasive positive pressure ventilator support) showing rhythmic electromyographic diaphragm burst activity, and FIG. 8B shows data from the same patient when placed on non-invasive positive ventilator support, showing suppression of all eDA.

DETAILED DESCRIPTION OF THE INVENTION

Figure 1:
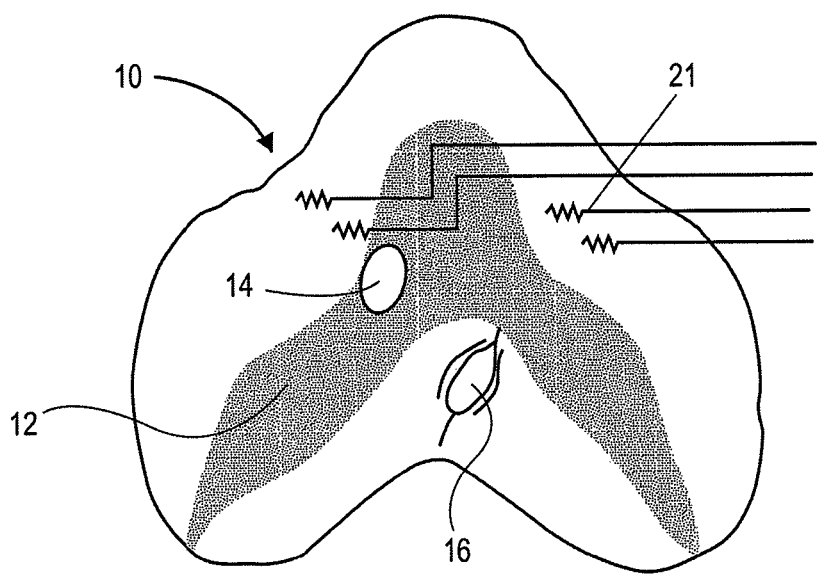
FIG. 1 provides an inferior view of a diaphragm and the placement of intramuscular electrodes therein.

Described here are devices, systems, and methods for identifying, tracking, or monitoring the presence or progression of neuromuscular disorders, particularly amyotrophic lateral sclerosis (ALS) and sleep apnea through the use of implanted electrodes that deliver electromyographic (EMG) data from neural motor points in the diaphragm. Intramuscular electrodes implanted chronically in muscle tissue can assess EMG activity continuously from the natural physiological drive of the patient (the term "patient" may refer to any subject or individual). The EMG may be analyzed by various approaches, including, for example, using threshold estimations, power density spectrum analysis, peak detection, motor unit estimation, or other methods to determine a consistent activity index for the target muscle. Any of these EMG-derived values may be used as a marker (biological marker, biomarker) for disease progression, either in a situation of deteriorating progression, or, more desirably, in an improving progression, as for example, a measure of the effectiveness of a treatment.

An example of a practical application is in the assessment of the course of disease progression in patients with a progressive neurodegenerative disease such ALS. These patients typically experience a progressive degradation of neurological function and usually die from respiratory complications. Diaphragm motor point EMG may be used to quantify the extent of diaphragm performance, failure of which is the leading cause of respiratory failure. Data derived from electrodes placed at the phrenic nerve motor point(s) in the diaphragm may provide a consistent and long-term measure of progression of the disease. The data may also be used to assess any improvement in physiological function as a result of a therapeutic intervention, such as may be supported by a device, a drug such as Riluzole, or somatomedin C, or an inhibitor or reactive oxygen species formation, or any other form of interventional therapy such as diaphragm pacing.

The patient may serve as his or her own control or point of reference. EMG data are collected over time from the same implanted electrodes, thus removing variation that may be associated with variation in location, or variation in electrode-electrode performance. Further providing control and consistency, as provided by embodiments of the invention, are methods by which data may be normalized or compared to other types of physiological data, as described below. Further, data over the time course of the disease process may be collected over similar spans of time, as defined, for example, by a single breath, a particular number of breaths, or a particular length of time, and by collecting data at the same time of day. For example, by monitoring motor point diaphragm EMG during sleep a consistent and dependable data pattern may be established. Alternatively, the EMG may be measured during a volitional maneuver (such as a sniff or a maximal inhalation), which may also be repeated with consistency. Correlation with other parameters, such as specific tidal volume, airway pressures, or abdominal pressures, may be used to further assess or normalize the EMG data to establish a broader baseline for comparison over time. These same types of analysis (particularly with appropriate volitional maneuvers) may be used in other muscles of the periphery to establish motor point EMG for other diseases or injuries that may be involved with a progressive degeneration.

Embodiments of the therapeutic or diagnostic method may include electrically mapping the target muscle (such as the diaphragm) to determine optimal location of placement at a neurological motor point. The motor point can be understood as the site where an electrical stimulus elicits an optimal diffuse contraction of the target muscle, rather than stimulating only the immediately-local muscle fibers, and this site is where the electrode is placed. In cases where an innervating nerve enters the muscle in distinct branches, there may be more than a single motor point for the muscle. For example, one motor point may elicit contraction of the anterior diaphragm while another elicits contraction of the posterior diaphragm. When such multiple motor points are identified, an intramuscular electrode may be implanted at each motor point, or in the case of a single motor point, electrodes may be placed in close proximity to each other.

The electrodes may be of monopolar, bipolar, or tripolar construction. When using bipolar or tripolar constructed electrode leads, each lead may be connected to a separate EMG amplifier. The electrode leads may exit the skin at an appropriate percutaneous exit site for connection to external EMG amplifiers and recorders. Alternatively, the electrodes may be connected to an implantable EMG amplifier and telemetered out of the body for analysis, either in real-time or for subsequent offline analysis.

Two monopolar electrodes may be implanted at phrenic nerve motor points and used to provide differential inputs to a bipolar EMG amplifier with a remote referenced indifferent electrode. These configurations allow monitoring of a large spatial area of the diaphragm, but also may be vulnerable to picking up additional EMG signal, such as from the heart. Alternatively, the electrodes may be configured referentially to a remote indifferent electrode, and the positive and negative inputs conveyed to a differential amplifier.

In another configuration, intramuscular monopolar electrodes may be implanted with bipolar contacts at a set distance between them. In this configuration, the electrode may be wound in a double helix, with each of the two multi-strand cables remaining electrically isolated. One particular embodiment of an intramuscular electrode is a double helix with the two multi-strand cables in electrical contact, creating a monopolar configuration (with redundancy). The bipolar configuration allows for a single implanted electrode to be connected to the amplifier and produce the ability to measure the muscle activity in a hemidiaphragm with more specificity than the two monopolar electrodes placed at varying distances. Additionally, this configuration, which has a repeatable set distance between contacts, may be used to build a population-based assessment of electromyographic activity based on stage of progression or severity of the disease.

A tripolar electrode configuration allows for better immunity from physiological "noise" such as may be derived from cardiac signals. By constructing the lead with three electrically isolated multi-strand cables wound in a tri-helical configuration, the tripolar electrode provides either an input to the positive amplifier input from the center element and input to the negative amplifier input with the two outer elements or a positive, negative, and reference (ground) input.

Thus, in monitoring ALS, this configuration of electrodes may be used as a comparison of diaphragm function that provides significantly more sensitivity than forced vital capacity (FVC) measurements, from implantation to survival. In central sleep apnea it may be used to assess the severity of diaphragm inactivity more specifically than oxygen desaturation. The bipolar configuration may also be used with or without the remote subcutaneous anode, as in the two monopolar electrode configuration.

Motor point electrodes may also be used to deliver either a therapeutic stimulus or a diagnostic stimulus. For example electrodes may be used to condition the diaphragm of an ALS patient with periodic recordings of EMG to determine the progression of the disease. As another example, motor point electrodes may be used to assess the progression of diaphragm deterioration or improvement following "resting" the diaphragm with non-invasive positive pressure ventilation. As another example, the electrode stimulus may be applied to one hemi-diaphragm and an EMG recorded in the contra-lateral hemi-diaphragm with any reflex response identified to analyze the integrity of reflex pathways or as an evoked response to determine the efficacy of an applied therapy. As yet another example, the EMG recording of abdominal muscles following a nerve anastomosis or surgical reconstruction, with or without stimulation therapy, may be used to promote regeneration or other type of applied therapy or drug intervention.

An example of a diaphragm motor point electrode and stimulation system is provided by the Synapse Biomedical NeuRx RA/4 DPS System. An example of an EMG amplifier and recorder is the Cleveland Medical Crystal PSG System.

Figure 2:
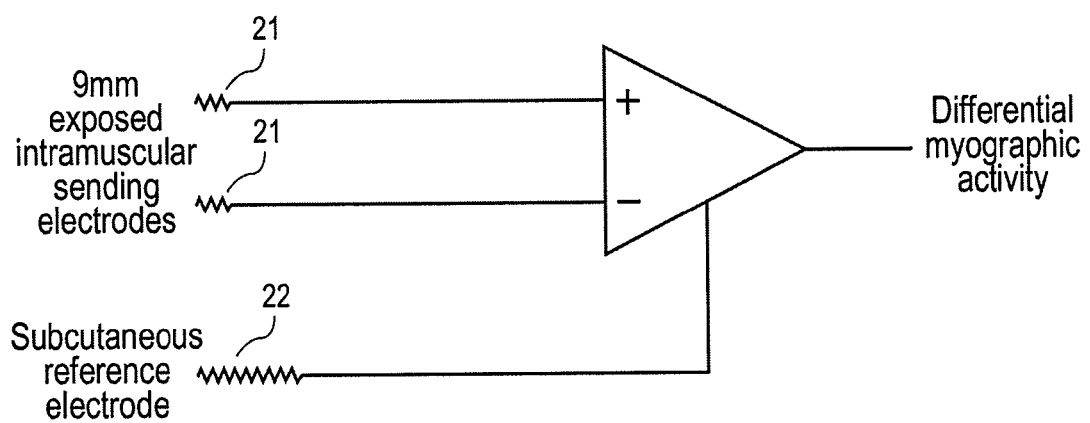
FIG. 2 is diagram of a representative circuit that includes positive and negative 9 mm sensing electrodes 21 and a subcutaneous reference 22 electrode from which differential myographic activity may be processed.

Turning now to illustrations, context, and examples of the general description of the method provided above, FIG. 1 provides an inferior view of a diaphragm 10, the central tendon of the diaphragm 12, the vena cava 14 shown within the tendon area, and the esophagus 16, dorsal to the tendon area. FIG. 2 provides a schematic view of two intramuscular monopolar electrodes 21 implanted at phrenic nerve motor points within the diaphragm. The method of mapping of motor points is described below in detail, and depicted a method flow diagram in FIG. 4.

FIG. 2 is diagram of a representative circuit that includes a positive and a negative 9 mm sensing electrode and a subcutaneous reference electrode from which differential myographic activity may be processed.

Figure 3:
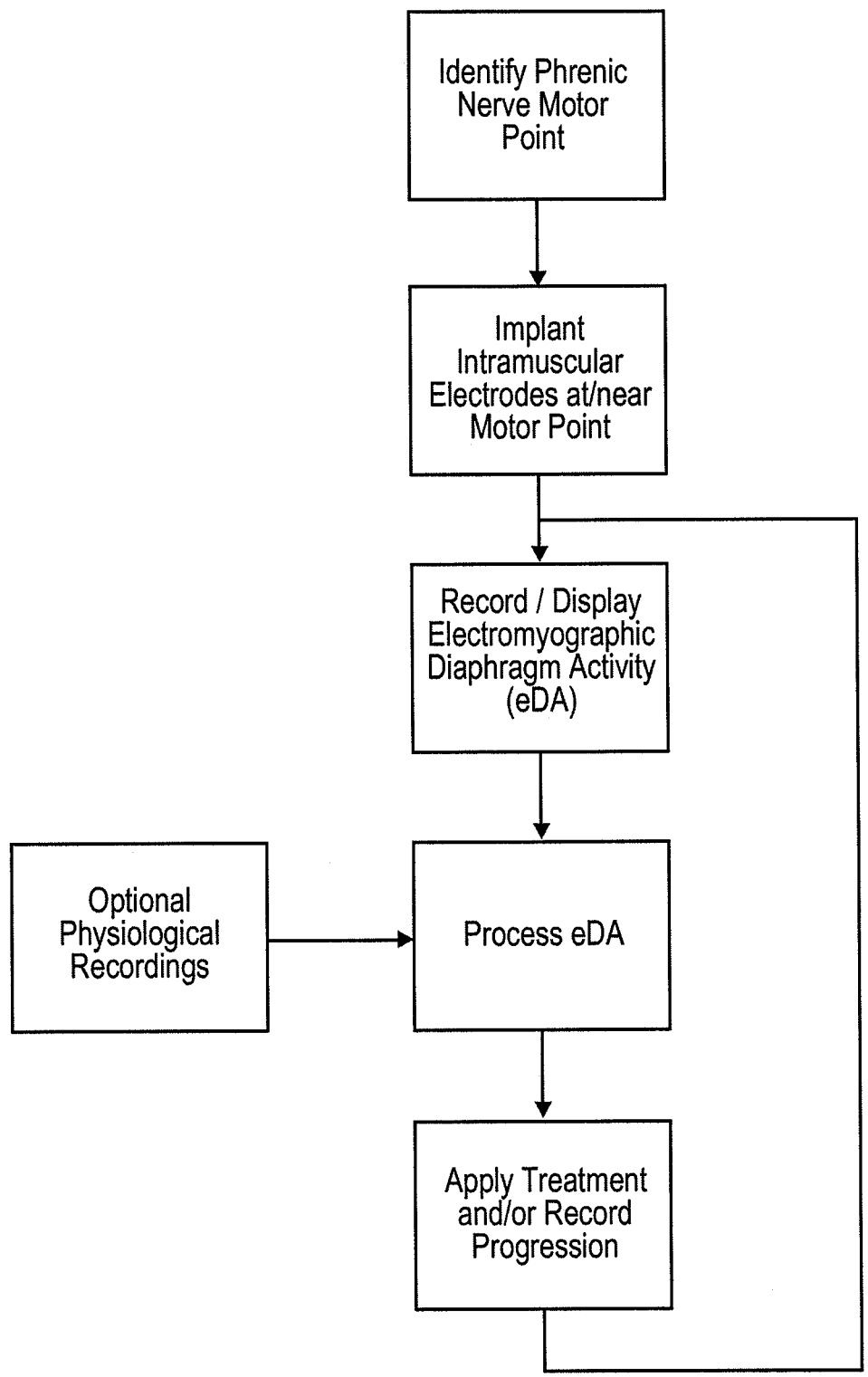
FIG. 3 is an overview flow diagram of the method of monitoring the level of a neurological disease affecting the diaphragm.

FIG. 3 is flow diagram that provides an overview of the method of monitoring the level of a neurological disease affecting the diaphragm. The method typically begins by identifying a phrenic nerve motor point and implanting an intramuscular electrode at or near that motor point. To be effective as a motor point electrode, the electrode needs to sufficiently near to the motor point such that stimulation of the diaphragm by that electrode elicits a diffuse response which is qualitatively different than the local area contraction elicited by stimulation of an electrode implanted at a typical non-motor point site. Following implantation of an electrode (or one or more electrodes) at a motor point, electromyographic diaphragm activity (eDA) data can be collected, recorded, and/or displayed. Systems and methods for the collection, recording, and displaying of eDA are described in detail in U.S. patent application Ser. No. 10/897,685 (titled "SYSTEM AND METHOD FOR CONDITIONING A DIAPHRAGM OF A PATIENT"), U.S. patent application Ser. No. 11/607,428 (titled "TRANSVISCERAL NEUROSTIMULATION MAPPING DEVICE AND METHOD"), U.S. patent application Ser. No. 11/716,475 (titled "VENTILATORY ASSIST SYSTEM AND METHODS TO IMPROVE RESPIRATORY FUNCTION"), and U.S. patent application Ser. No. 11/716,459 (titled, "VENTILATORY ASSIST SYSTEM AND METHODS TO IMPROVE RESPIRATORY FUNCTION"), all of which are incorporated in their entirety by this reference.

Figure 5:
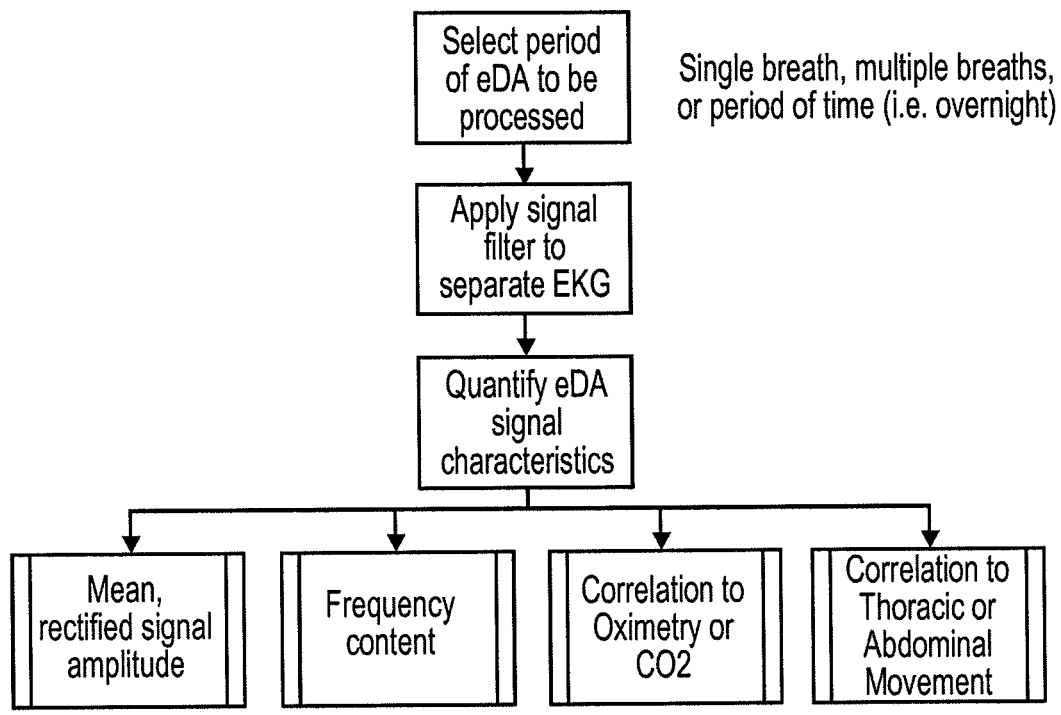
FIG. 5 is a flow diagram of the method of processing electromyographic diaphragm activity into disease level diagnostic information.

Following the collection of eDA data, the data are processed, as described in greater detail below and as depicted in FIG. 5. Other physiological data may be incorporated into the processing of eDA data, as also described below and depicted in FIG. 5.

Figure 4:
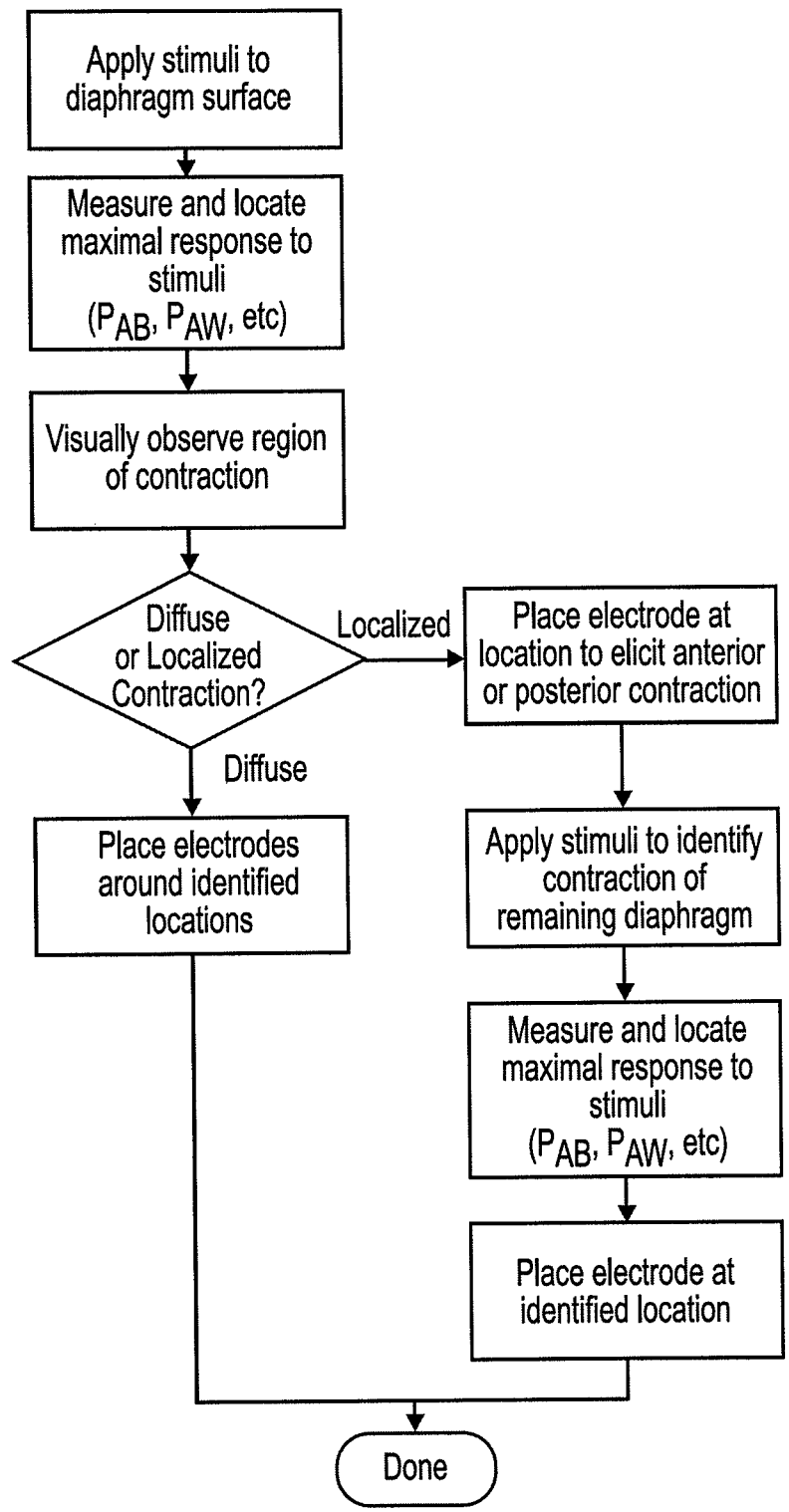
FIG. 4 is a flow diagram of the method of mapping a diaphragm motor point site prior to making use of electrodes planted at the site to monitor the level of disease.

FIG. 4 is a flow diagram that provides a more detailed view of the method of mapping a diaphragm motor point site prior to making use of electrodes planted at the site to monitor the level of disease. Embodiments of the method include applying electrical stimuli with electrodes to the surface of the diaphragm. In attempting to locate a motor point, the method may include applying stimuli to multiple sites and identifying or locating the site within an area that gives a maximal response among the nearby sites. The response may be measured, for example, by abdominal pressure response ($P_{AB}$) response or airway pressure ($P_{AW}$) response. The method further includes determining the maximal attainable response at that most responsive site; this is obtained by repeated stimulation until there is confidence that the maximal stimulation from the most responsive site has been attained. This value, when taken at an initial or early stage in the evaluation of a patient is important because it forms the baseline response against which progression of the disease over time is compared.

The method then may further include visual observation of the response of the diaphragm to the stimulus, and to verify that the response is that characteristic of a motor point stimulation which includes a broad diffuse response, in contrast to a localized response that is characteristic of stimulating a nerve at a site other than a motor point. In the event that a diffuse contraction is elicited by stimulation at the candidate site, it may be concluded that the site is a motor point, and intramuscular electrodes are implanted at the site.

In the event that the contraction response to stimulation of the candidate site, instead, is a localized contraction, the earlier mapping steps may be repeated. Typically, if a local contraction is elicited, it is a branch of the phrenic nerve that has been localized, not the main trunk. The nerve branch may, for example, innervate only one of the anterior or posterior portions of the diaphragm. Thus, stimuli may be provided to identify contraction of the remaining portion of the diaphragm. As described earlier, the method may include applying stimuli to multiple sites and identifying or locating a site within the local area that gives a maximal response as measured, for example, by $P_{AB}$ or $P_{AW}$. The method further includes determining the maximal attainable response at that most responsive site, and then implanting an intramuscular electrode at the identified site.

FIG. 5 is a flow diagram of the method of processing electromyographic diaphragm activity into disease level diagnostic information. The method includes selecting an appropriate period of time over which eDA will be collected for comparison at an initial observation point and then at later observation points. Such time periods may be, for example, a single breath, a particular number of breaths, or a particular length of time (in which a variable number of breaths may occur). The method then includes collecting and recording the eDA data and applying any appropriate processing, such as filtering out electrical activity derived from sources other than the diaphragm, in particular EKG data. The method further includes quantifying eDA signal characteristics to represent the observation time point, such as mean rectified signal amplitude or frequency content. Additional optional steps may include correlating the eDA signal characteristics with other physiological data that are symptomatic of the disease, such as blood levels of oxygen or carbon dioxide, or bodily movements, such as movement of the thorax or abdomen.

Figure 6A:
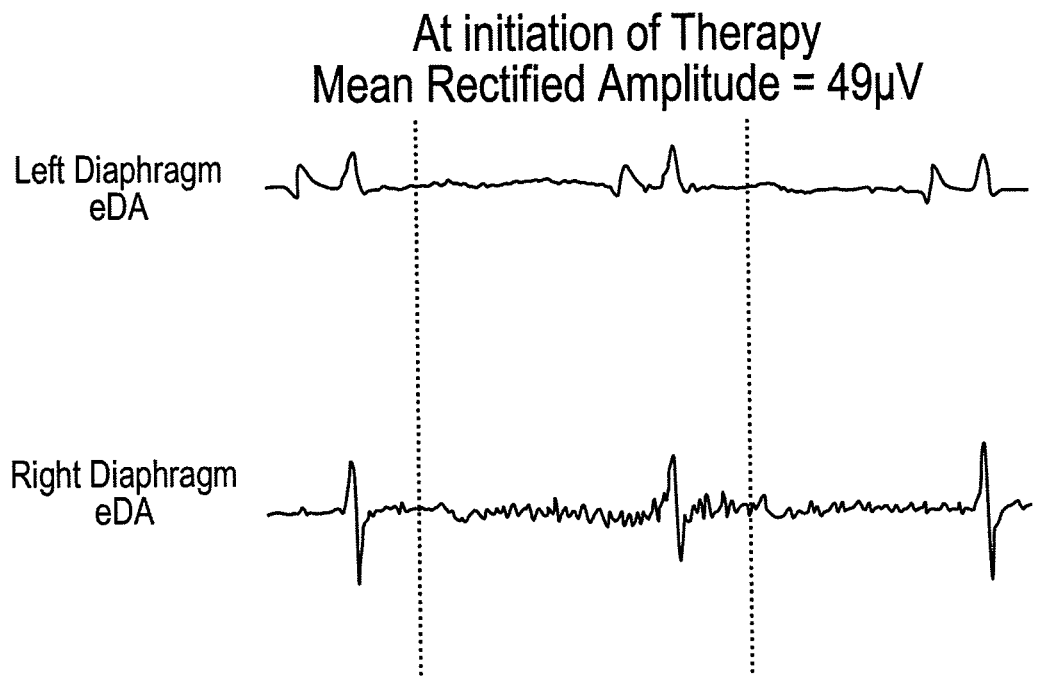
FIGS. 6A and 6b provide electromyographic diaphragm activity (eDA) data from a patient prior-to and after receiving diaphragm pacing therapy.
Figure 6B:
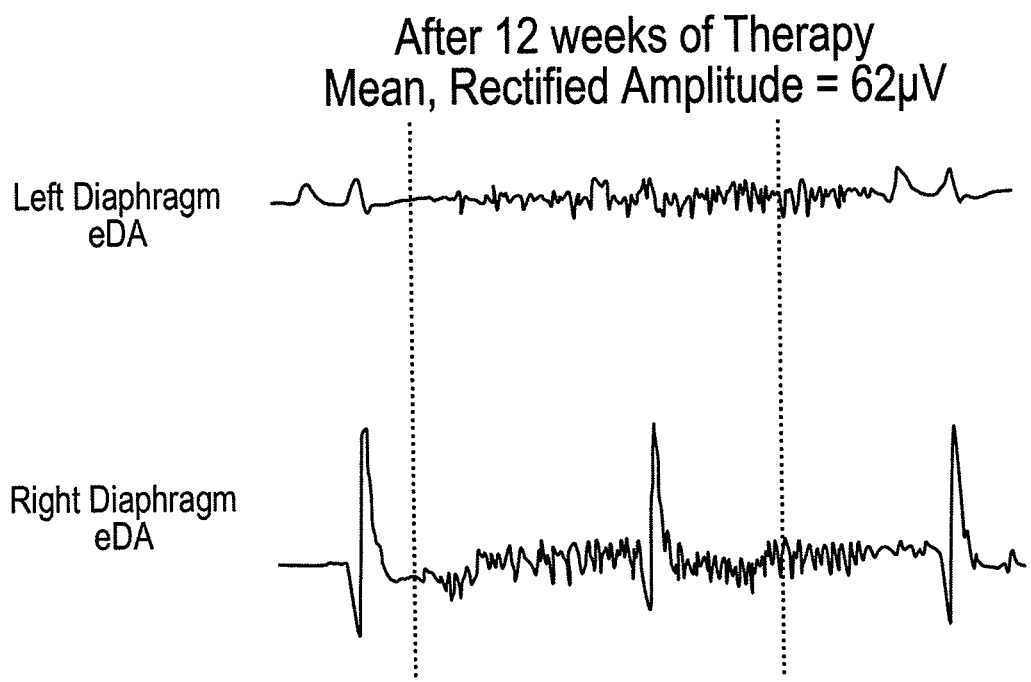

FIGS. 6A and 6b provide electromyographic diaphragm activity (eDA) data from a patient prior-to and after receiving diaphragm pacing therapy. FIG. 6A shows the right diaphragm of the patient having a mean rectified amplitude of 49 µV at the initiation of therapy, and FIG. 6B shows the right diaphragm of the patient having a mean rectified amplitude of 62 µV after 12 weeks of therapy. The data may be interpreted as an improvement in status. The mean amplitude is but one feature of the EMG that can be used to compare data from the same electrodes over time. In this example, the increase in amplitude may correlate to diaphragm activity and health (e.g., movement of the diaphragm). The EMG from the same electrode, in the same position of the diaphragm, over weeks of therapy provides a sensitive and reliable marker, particularly in comparison to other methods such as fluoroscopy.

The mean amplitudes illustrated in FIGS. 6A and 6B are referenced with respect to the individual patent into which the electrode(s) from which the traces are recorded has been implanted. Thus, recordings made at different times from the same patient may be compared directly. In some variations, it may be desirable to determine population data or norms for patient so that parameters may be compared across patients. For example, ranges of values (normal values) could be determined by population studies. Normal values may be based on index values (e.g., some combination of parameters, which may include amplitude, frequency, etc.). Normal values may also be based on combining additional inputs, such as lung volume, patient age, size, overall activity of the diaphragm based on the mapping, etc.

Figure 7:
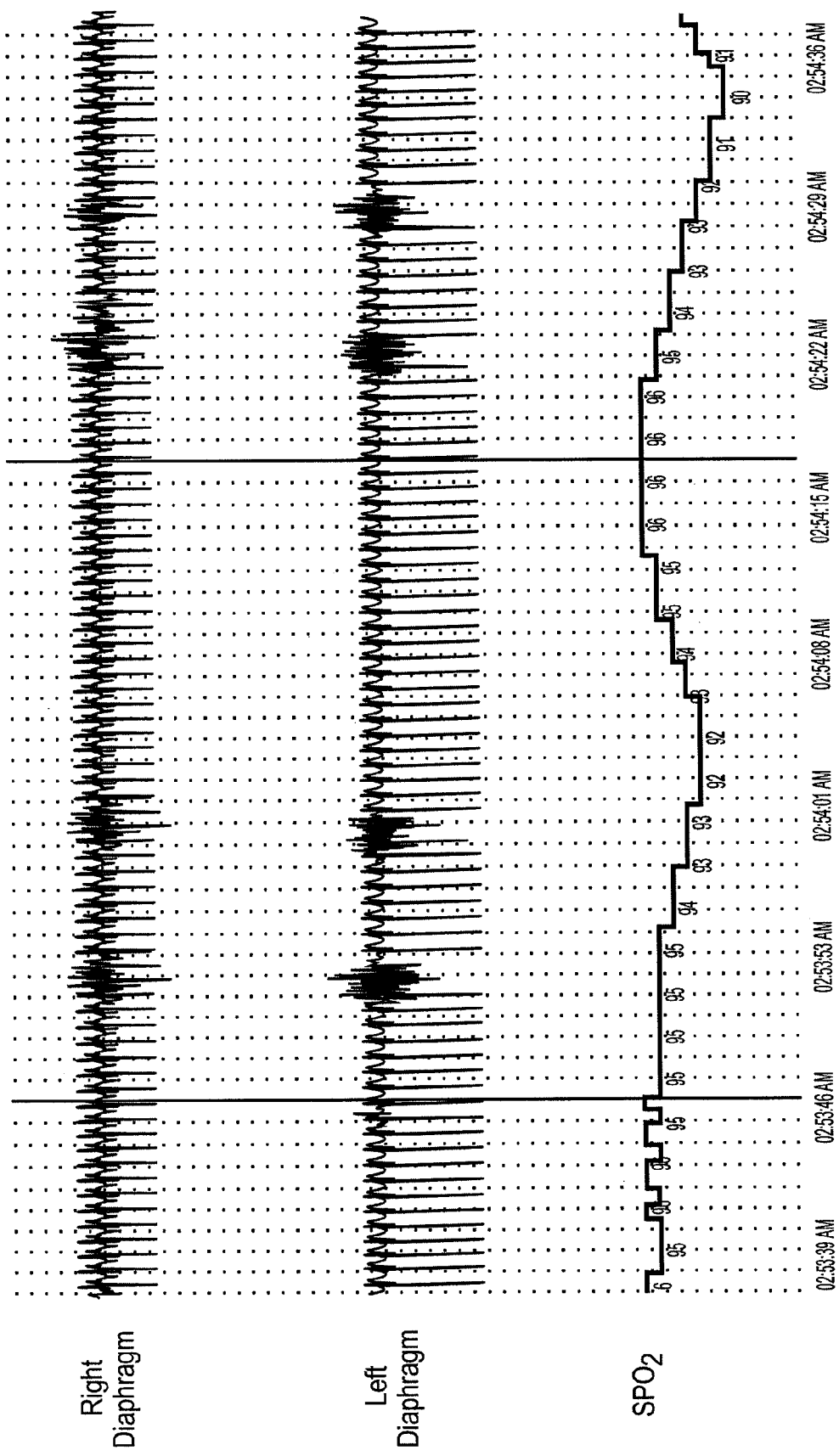
FIG. 7 provides EMG data from the right and left diaphragm of a patient and the level of saturation of peripheral oxygen ($SpO_2$) of a patient, the data being diagnostic of a sleep disorder.

FIG. 7 provides EMG data from the right diaphragm (upper trace), left diaphragm (middle trace), and $SpO_2$ (lower trace) of a patient, in which level of saturation of peripheral oxygen ($SpO_2$) of a patient is diagnostic of a sleep disorder. The data provide a view of a one-minute snapshot of breathing (from 2:53:39 a.m. to 2:54.39 a.m.); during this time interval there are typically be several breaths spaced out over the period. An apnea is defined as the cessation of breathing for 10 or more seconds. Another indicator of sleep-disordered breathing is a decrease of the oxygen saturation ($SpO_2$) of 3-4%, as seen in this trace as twice dropping to levels between about 90% and 92% saturation. Breathing is indicated by the bursts of diaphragm electromyographic actions; there are four distinct breaths in two pairs that are representative of Cheyne-Stokes breathing. It can be seen that there is an apnea event at the beginning of the data set (at least 14 seconds without a breath prior to the first pair of diaphragm actions). This apnea is associated with an hypopnea as seen in the $SpO_2$ tracing (note there is a sensing delay of several seconds of between the actual occurrence of a desaturation and the sensed display using finger pulse oximetry—displayed on the $SpO_2$ tracing). There is then another apnea event between the two pairs of diaphragm activity and an associated hypopnea, with the delayed appearance, as above. After the second pair of activity events, there also appears to be another apnea (although the time is cut at 9 seconds). This rate of about three apnea events per minute represents about 180 apneas per hour (if the breathing continued in this manner), which is a severe sleep apnea. Also, these data clearly demonstrate the apnea to be of central origin (i.e., central sleep apnea) as there is an absence of centrally-mediated diaphragm activity.

FIGS. 8A and 8B shows electromyographic diaphragm activity (eDA) data from a patient both prior to and after receiving non-invasive ventilatory therapy. FIG. 8A shows data from the patient showing rhythmic eDA while the patient is breathing and not on positive pressure ventilation, and FIG. 8B shows data from the same patient when placed on positive pressure ventilation showing complete loss of eDA. This illustrates the ability of the system to assess eDA and the effects on eDA with other therapies such as positive pressure ventilation. In this case, positive pressure ventilation is negatively affecting diaphragm activity by suppressing respiratory drive.

The non-invasive ventilatory (NIV) therapy described above refers to the use of BiPAP. The two traces in FIGS. 8A and 8B were done consecutively (i.e. minutes apart). These traces illustrate the presence of diaphragm activity without NIV, and the absence of diaphragm activity with the application of NIV (i.e. BiPAP). This provides evidence of therapy (in this case NIV) affecting diaphragm function.

Systems

Figure 9:
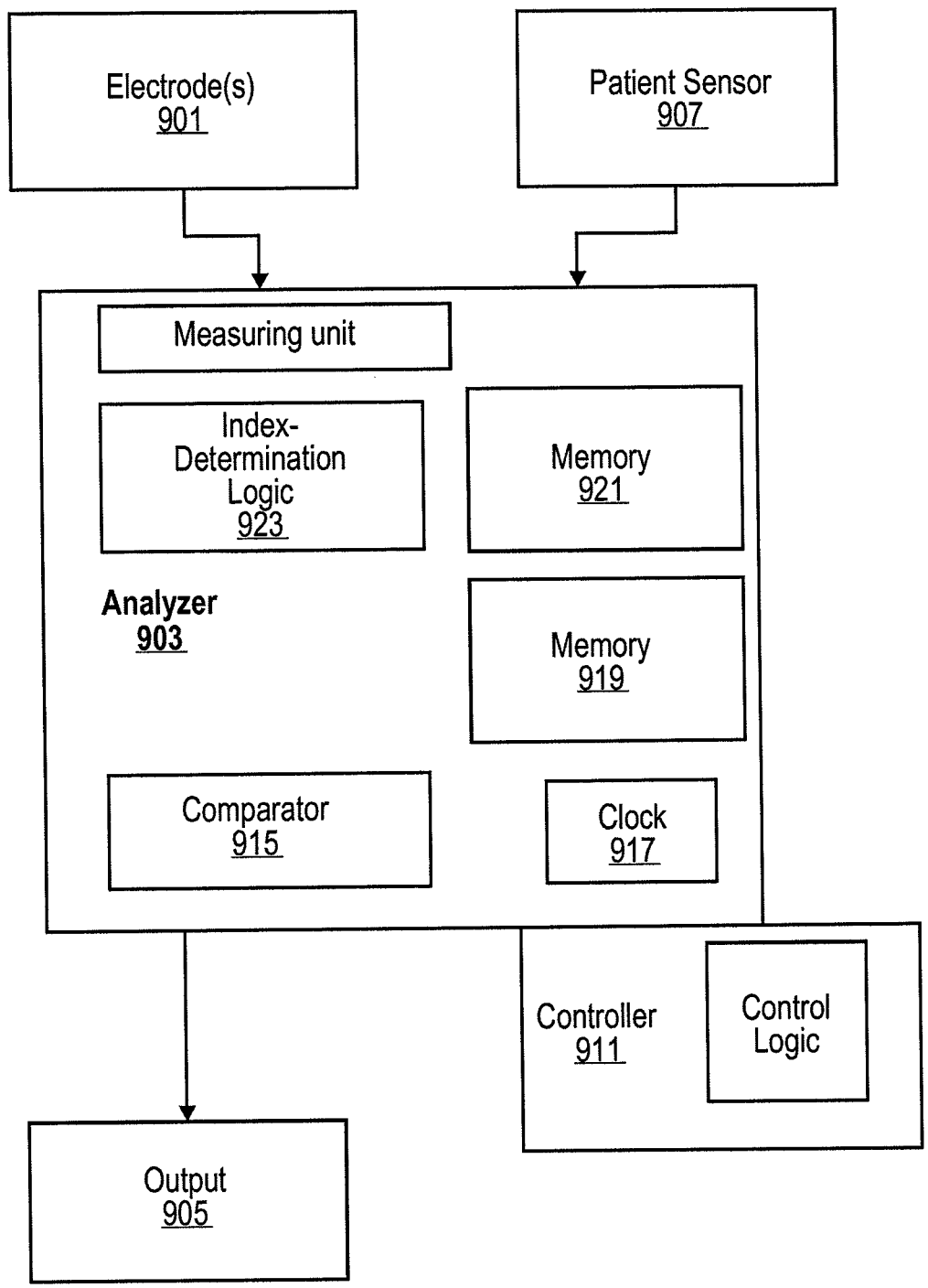
FIG. 9 is a schematic illustration of a system for diagnosing or tracking the progression or treatment of a neurological disorder that affects the function of a diaphragm.

FIG. 9 illustrates one variation of a system 900 for diagnosing or tracking the progression or treatment of a neurological disorder that affects the function of a diaphragm. In general, a system may include one or more implantable diaphragm electrodes 901, an analyzer 903 to receive EMG data from the electrode(s) at different times, wherein the analyzer is configured to determine a "score" (e.g., an activity score) based on the comparison of the EMGs taken from the same electrodes over time.

The electrodes 901 may be any of the electrodes previously described. For example, one or more monopolar electrodes, bipolar electrodes, or tripolar electrodes may be used. These electrodes may be configured for implantation into a patient at or near the patient's diaphragm. Thus, the electrodes(s) may include one or more anchors for holding the electrodes in position. For example, the electrodes may be hooked or barbed. The electrode(s) may communicate with the analyzer. For example, the electrodes may be wired or wirelessly connected to the analyzer.

An analyzer typically includes index-determining logic 923, which may be software, hardware, or some combination thereof. For example, the analyzer may include one or more processors (general or dedicated) configured to run the index-determining logic 923. The index-determining logic 923 receives EMG data from the electrode(s) 901 and measures one or more parameters from the EMG signal in order to determine an index which can be stored and later compared to an EMG signal at a later time (by comparing to an index of the EMG signal from the later time). Any relevant parameter may be measured and used to contribute toward the index. In some variations, more than one parameter may be measured, and may contribute towards the calculation of the index. Parameters that may be measured include: amplitude, frequency, power spectrum, time-to-peak rise time, relaxation time, compound action potential rise time, compound action potential fall time, fast twitch muscle contribution, and slow-twitch muscle contribution. Thus, the analyzer 903 may include EMG signal processing modules for analyzing the EMG signal(s) from the electrode(s) 901. The analyzer 903 may also include EMG signal conditioners for conditioning the EMG signal before measuring from it. For example, the signal may be filtered (e.g., to remove undesirable signals such as ECG signals or other noise), smoothed, transformed (e.g., Fourier transformation, etc.), or otherwise conditioned.

The index-determining logic 923 may also include one or more inputs from other sensors affiliated with the patient or patient. For example, the index-determining logic may receive inputs from one or more sensors 907. A patient sensor (which may be referred to as simply a sensor) 907 may be a pressure sensor, a motion sensor, a temperature sensor, or the like. For example, a sensor may measure tidal volume, airway pressure, or abdominal pressure. This data may be measured simultaneously or sequentially with the EMG at a particular time, and may be used by the index-determining logic 923 to calculate or otherwise determine an index at the predetermined time period.

One or more memory modules 921, 919 may also be included as part o the analyzer 903. The memory may be used to store EMG signals for later analysis, and/or indexes calculated (at least in part) from an EMG signal. The memory maybe read/written by other parts of the analyzer, including the index-determining logic 923, a controller 911, a comparator, 915, etc.

In particular, a comparator 915 may be used to compare two or more indexes. The comparator may output an activity score, which may indicate the presence, progression or treatment effect of a neurological (e.g., neuromuscular) disorder on the patient. In some variations a comparator is not used, and the system outputs the individual indexes.

The analyzer may also include, or communicate with, a controller 911 which includes control logic for controlling the activity of the analyzer or any of the other components of the system. For example, a controller may be used to control the system to acquire a first EMG signal at a first time. As described herein, the first sample (EMG) may be taken for a predetermined time period at a predetermined time. In some variations the EMG sample is taken for one respiratory cycle, or a portion of a respiratory cycle, or during a single breath or a portion of a breath, etc. The controller may also control the acquisition of patient sensor data, and coordinate the patient sensor data acquisition and the measurement of the EMG. The controller may also trigger the acquisition of the second (or more) EMG signals.

A clock 917 may be included as either part of the analyzer or part of the controller, or some other part of the system, and communicate with the controller and/or analyzer. The clock may be useful for determining the length of the data acquisition and the time between signal collection periods.

In some variations, the system includes an output 905, including a display. Any appropriate output may be used, including visual outputs (screens, projections, indicator lights, LEDs, etc.), audible outputs (sounds, buzzers, etc.), and the like. In some variations, the output is a monitor, printer, or display. The output may be a digital medium (memory, disk, internet, etc.).

A system for diagnosing, tracking the progression of a disease state, and/or for tracking the efficacy of a treatment may also include additional elements not shown in the schematic FIG. 9, thus, these elements are not exclusive. Furthermore some of these elements may be omitted. In some variations, the interconnection or element may be different than shown here. Furthermore, elements shown in FIG. 9 may be combined. For example, the comparator 915 may be incorporated as part of the index-determining logic 923.

Method

Figure 10:
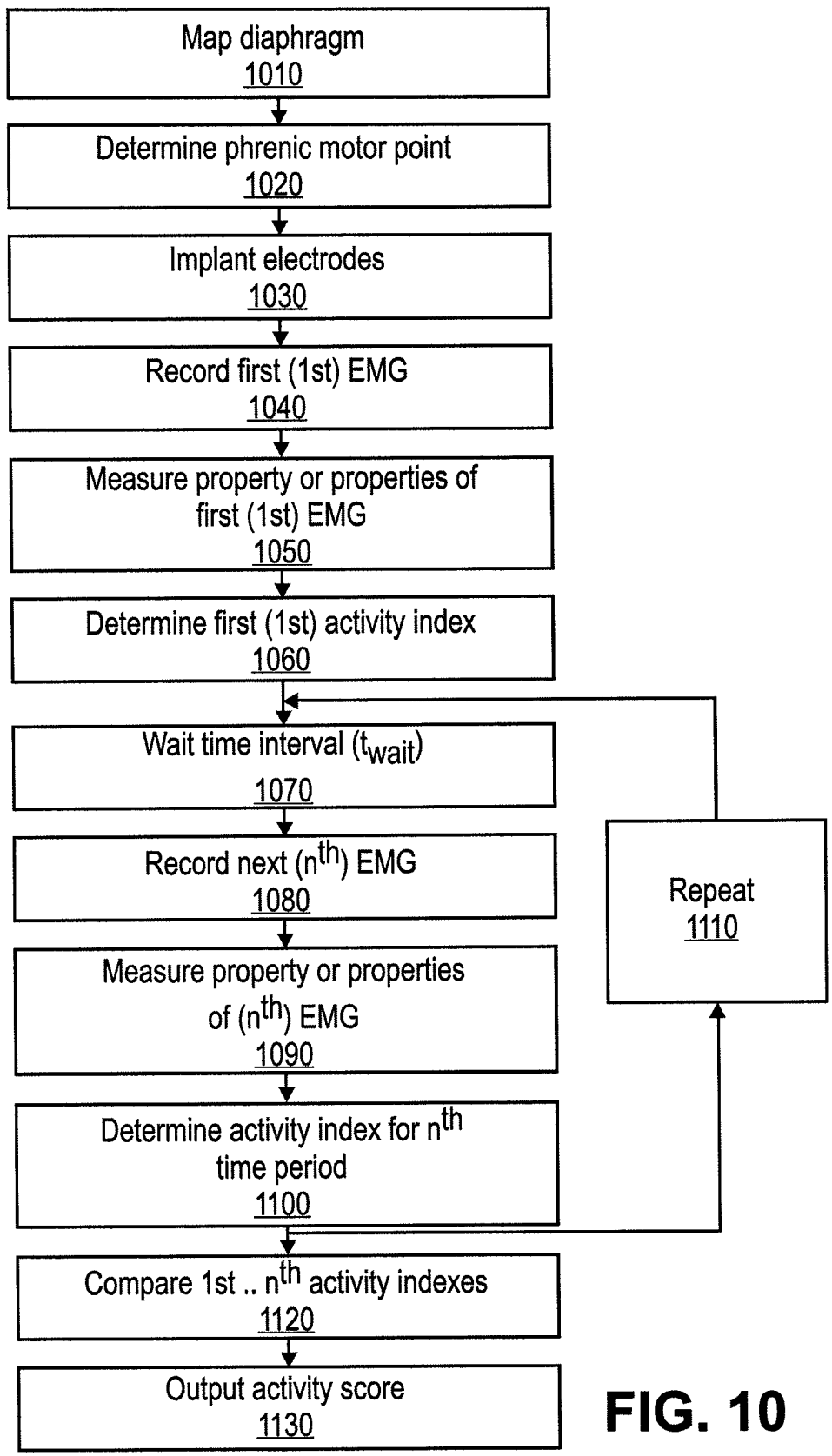
FIG. 10 illustrates one variation of a method of diagnosing or tracking the progression or treatment of a neurological disorder that affects the function of a diaphragm.

In addition to the methods described above, an exemplary method of diagnosing or tracking the progression or treatment of a neurological disorder that affects the function of a diaphragm are schematically illustrated in FIG. 10. In general, a method of diagnosing or tracking progression or treatment of a disorder (and particularly neuromuscular disorders such as ALS) may include the steps of detecting a first EMG signal at a first time 1040, waiting some interval (e.g., typically hours, days, weeks or months) 1070, and then detecting a second EMG signal at a second time 1080, and then comparing an index of each of the two EMG signals which may be measured from one or more features of the EMG signal.

FIG. 10 illustrations one variation of a method of diagnosing or tracking the progression or treatment of a neurological disorder that affects the function of a diaphragm. Certain of the steps illustrated in FIG. 10 may be omitted, and one or more additional steps may be added to this method. In the example, of FIG. 10, the first step is the proper placement of the electrode(s) used to determine the diaphragm EMG signals. In general, this step may require mapping of the diaphragm 1010, as previously described. In particular, mapping may be used to determine what parts of the diaphragm are electrically active or viable. This may be especially helpful in monitoring ALS patients (or suspected ALS patients) in whom parts of the diaphragm may be damaged so that they no longer respond and/or propagate electrical signals from the nerves. Thus it would be difficult or impossible to get a viable EMG without first mapping the electrically active regions. In some variations, the mapping may also identify phrenic motor nerve points, as mentioned above.

In conjunction with the mapping steps 1010, 1020, the diaphragm electrode(s) may be inserted or implanted 1030 based on the results of the mapping. For example, after mapping a phrenic nerve motor point, an electrode may be implanted so that it receives (and/or sends) electrical signals or EMG signals.

After successful implantation (which may be tested), the electrode may be used to detect an EMG from the diaphragm. The signal may be coordinated with other sensors (such as the patient sensors previously described). An index (activity index) may then be measured 1060 using one or more features measured 1050 from the first EMG. If patient sensors are also used, this data may be combined in some way with the measurements taken from the EMG. For example, an index may be a measure of the frequency, amplitude, etc., of the EMG that is weighted by (or otherwise combined with) a measure of tidal volume. The determined activity index for this first time interval may be stored for later output and/or comparison. Additional information (e.g., the time, actual EMG and/or additional data) may also be stored with it, and may be used to inform the comparison and/or display of the index with other activity indexes.

After some appropriate time interval, the process of detecting an EMG is repeated. Any appropriate time interval may be used, particularly time intervals longer than hours, days, weeks, months or even years. The time interval may be predetermined (e.g., preset) or it may be triggered. For example, a patient or doctor may manually trigger the end of the time interval and detect and analyze an EMG 1080, from which an activity index 1100 can be calculated.

Multiple (n) activity indexes can be determined, for comparison and/or display, by repeating this process 1110. Comparing the indexes 1120 may be used to score the change in activity indexes. For example, a score may be a percent change, a rate of change, a graphic comparison, a linear regression, or the like, to indicate differences between the diaphragm state at the initial and later time points.

One or more outputs may be provided, outputting any of the activity indexes, EMGs, and/or the activity score. For example, the output may be a monitor which can be viewed. In some variations, the output is a digital medium such as a memory, output port, or the like.

As mentioned, the method described above is only one example of a method of determining diaphragm health, and other variations are possible. The method may be particularly useful for any of (1) diagnosing a disease affecting the diaphragm, (2) tracking the progression of a disease affecting the diaphragm, or (3) tracking the efficacy of a treatment of a disease affecting the diaphragm. For example, the methods described herein may be applied as a method of tracking the treatment of ALS.

Although the foregoing invention has been described in some detail by way of illustration and example for purposes of clarity of understanding, it will be readily apparent to those of ordinary skill in the art that certain changes and modifications may be made thereto without departing from the spirit or scope of the invention, and the claims thereto.

What is claimed is:

1. A method of diagnosing or tracking the progression or treatment of a neurological disorder that affects the function of a diaphragm, the method comprising:

measuring a first EMG signal during a volitional breathing maneuver at an initial recording time before the start of therapy from one or more electrodes chronically implanted in a diaphragm;

measuring a second EMG signal from the same one or more electrodes at a later recording time during a volitional breathing maneuver after the start of the therapy; and comparing one or more characteristics of the first EMG signal and the second EMG signal and characterizing the presence, progression or treatment of a neurological disorder based on the comparison.

2. The method of claim 1, wherein the disorder comprises any of a centrally-mediated breathing disorder or a neurodegenerative disease.

3. The method of claim 1, wherein the comparing step comprises comparing one or more of amplitude, frequency, power spectrum, time-to-peak rise time, relaxation time, compound action potential rise time, compound action potential fall time, fast twitch muscle contribution, and slow-twitch muscle contribution.

4. The method of claim 1, further comprising:
mapping the diaphragm to determine an active region of the diaphragm; and
implanting the one or more electrodes at an active region of the diaphragm.

5. The method of claim 1, further comprising:
mapping the diaphragm to determine a phrenic nerve motor point of the diaphragm; and
implanting the one or more electrodes at the phrenic nerve motor point.

6. The method of claim 5, wherein the mapping step includes applying electrical stimuli to an area of diaphragm surface and identifying a site within the area that provokes a maximal physiological response to the stimuli.

7. The method of claim 6, wherein the mapping step includes observing a physiological response to the stimuli including any of: abdominal pressure or airway pressure, and diaphragm contraction.

8. The method of claim 1, wherein measuring the first EMG signal comprises:
selecting a duration and/or period of time for collection, wherein the duration and/or period of time for collection for the first EMG signal is the same for the second EMG signal; and
quantifying at least one characteristic of the EMG signal over the selected time.

9. The method of claim 8, wherein the time duration of collection of the EMG signal is selected from the group consisting of: a single breath and a particular number of breaths.

10. The method of claim 8, wherein the characteristic of the EMG signal quantified is selected from the group consisting of: amplitude, frequency, power spectrum, time-to-peak rise time, relaxation time, compound action potential rise time, compound action potential fall time, fast twitch muscle contribution, and slow-twitch muscle contribution.

11. The method of claim 1, wherein the steps of measuring the first EMG signal and measuring the second EMG signal comprises filtering the EMG signals to remove or reduce electrical signals not arising from the diaphragm.

12. The method of claim 1, further comprising correlating the EMG signals with a measurement of another physiological parameter.

13. The method of claim 12, wherein the physiological parameter comprises one or more blood gas level, airway pressure, abdominal pressure, and abdominal movement.

14. A method of diagnosing or tracking the progression or treatment of a neurological disorder that affects the function of a patient's diaphragm, the method comprising:
determining a first activity index from a patient's diaphragm motor point EMG at a first time during a volitional breathing maneuver before the start of a therapy, wherein the first activity index is a first measure of a first component of the EMG that is combined with a first measure of a respiratory parameter value;
determining a second activity index from the patient's diaphragm motor point EMG at a second time during a volitional breathing maneuver after the start of the therapy, wherein the second activity index is a second measure of the first component of the EMG that is combined with a second measure of the respiratory parameter value;
comparing the first activity index and the second activity index; and
characterizing the presence, progression or treatment of a neurological disorder based on the comparison between the first activity index and the second activity index,
wherein the first activity index and the second activity index are determined from a chronically implanted electrode for measuring the patient's diaphragm motor point EMG at a first time and at a second time.

15. The method of claim 14, further comprising mapping the patient's diaphragm to determine a phrenic nerve motor point.

16. The method of claim 14, further comprising implanting a diaphragm electrode in or adjacent to the patient's diaphragm at a phrenic nerve motor point.

17. The method of claim 14, wherein first and second activity indexes are determined based at least in part on one or more of: amplitude, frequency, power spectrum, time-to-peak rise time, relaxation time, compound action potential rise time, compound action potential fall time, fast twitch muscle contribution, and slow-twitch muscle contribution.

18. The method of claim 14, wherein the volitional maneuver is a sniff or a maximal inhalation.

19. The method of claim 14, wherein the respiratory parameters are selected from the group consisting of: tidal volume, airway pressure, abdominal movement, abdominal pressure, and blood gas level.

20. The method of claim 1, further comprising determining and presenting a score based on the comparison.

21. The method of claim 14, further comprising determining and presenting a score based on the comparison.

22. The method of claim 21, wherein the score indicates a degree of change between the first activity index and the second activity index.

23. The method of claim 8, wherein the time duration of collection of the EMG signal is during a predetermined portion of the respiratory cycle.

24. The method of claim 14, wherein the first time and the second time are separated by a predetermined time interval of at least one hour.

25. The method of claim 14, wherein the first time and the second time are separated by a predetermined time interval of at least one day.

26. The method of claim 14, wherein the first time and the second time are separated by a predetermined time interval of at least one week.

27. The method of claim 14, wherein the first time and the second time are separated by a time interval with an end that is manually triggered.

28. The method of claim 14, wherein the respiratory parameter value is a tidal volume.

\* \* \* \* \*